US011346834B2

(12) United States Patent
Rampfl

(10) Patent No.: US 11,346,834 B2
(45) Date of Patent: May 31, 2022

(54) METHOD AND SYSTEM FOR CHECKING AN OIL FOR AN INTERNAL COMBUSTION ENGINE, IN PARTICULAR OF A MOTOR VEHICLE

(71) Applicant: Bayerische Motoren Werke Aktiengesellschaft, Munich (DE)

(72) Inventor: Michael Rampfl, Grosskarolinenfeld (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 121 days.

(21) Appl. No.: 16/821,340

(22) Filed: Mar. 17, 2020

(65) Prior Publication Data
US 2020/0217832 A1 Jul. 9, 2020

Related U.S. Application Data

(63) Continuation of application No. PCT/EP2018/073347, filed on Aug. 30, 2018.

(30) Foreign Application Priority Data

Sep. 21, 2017 (DE) .................... 10 2017 216 729.7

(51) Int. Cl.
*G01N 33/30* (2006.01)
*G01N 11/00* (2006.01)
(52) U.S. Cl.
CPC ............ *G01N 33/30* (2013.01); *G01N 11/00* (2013.01); *G01N 2011/0026* (2013.01)
(58) Field of Classification Search
None
See application file for complete search history.

(56) References Cited

U.S. PATENT DOCUMENTS

2006/0027486 A1 2/2006 Rosenbaum et al.
2008/0140366 A1* 6/2008 Gao ................. G01N 31/00
703/2

(Continued)

FOREIGN PATENT DOCUMENTS

DE      297 708 A5    1/1992
DE     41 31 969 A1   4/1993
(Continued)

OTHER PUBLICATIONS

S. W. Rein, D. L. Alexander, S. A. Cryvoff and M. A. Dahlstrom. Investigations of Engine Oil Shear Stability in Laboratory Tests and Road Tests. SAE Transactions vol. 96, Section 7: Fuels and Lubricants (1987), pp. 749-760 (Year: 1987).*

(Continued)

*Primary Examiner* — Paul M. West
*Assistant Examiner* — Mark A Shabman
(74) *Attorney, Agent, or Firm* — Crowell & Moring LLP

(57) ABSTRACT

A method for checking an oil as a lubricant for an internal combustion engine includes: performing a laboratory test in which, independently of the internal combustion engine, a three-dimensional temperature-viscosity-shear rate characteristic field which characterizes the oil is determined, which includes a plurality of viscosities, shear rates and temperatures of the oil determined experimentally by the laboratory test and in each case associates shear rates and viscosities with the temperatures; checking whether the temperature-viscosity-shear rate characteristic field meets at least one predeterminable first criterion; and if the temperature-viscosity-shear rate characteristic field meets the first criterion: performing at least one test bench trial in which, via the internal combustion engine, it is checked whether the oil meets at least one predeterminable second criterion.

8 Claims, 3 Drawing Sheets

(56) References Cited

U.S. PATENT DOCUMENTS

2011/0003725 A1     1/2011   Matsui et al.
2016/0289591 A1*   10/2016   Fujiwara ............ C10M 169/041

FOREIGN PATENT DOCUMENTS

| DE | 199 59 145 C2 | 6/2001 |
| DE | 10 2005 057 077 B4 | 6/2006 |
| DE | 10 2008 041 100 A1 | 2/2010 |
| DE | 10 2008 053 077 A1 | 5/2010 |

OTHER PUBLICATIONS

Kumbár, V., Polcar, A., & Čupera, J. (2013). Rheological profiles of blends of the new and used motor oils. Acta Univ. Agric. Silvic. Mendel. Brun., 61(1), 115-121. doi: 10.11118/actaun201361010115 (Year: 2013).*

PCT/EP2018/073347, International Search Report dated Dec. 20, 2018 (Three (3) pages).

German Search Report issued in German counterpart application No. 10 2017 216 729.7 dated Jul. 3, 2018, with Statement of Relevancy (Six (6) pages).

Nadooshan et al., "Evaluation of rheological behavior of 10W40 lubricant containing hybrid nanomaterial by measuring dynamic viscosity", *Physcia E—Low-Dimensional Systems and Nanostructures*, NL, vol. 92, May 19, 2017, pp. 47-54, XP055530102.

Kirschke, "Phenomena of high polymer solutions while flowing through capillaries at high rates of shear", *Rheologica Acta.*, DE, vol. 21, No. 4-5, 1982, pp. 508-510, XP055530123.

Sikora et al., "Viscosity in Exploitation Time Analysis of the Lubricating Oil Used in the Combustion Engine of the Personal Car", *Diffusion and Defect Data.*, CH, vol. 220-221, Jan. 2015, pp. 271-276, XP055530112.

English-language Chinese Office Action issued in Chinese application No. 201880054758.X dated Nov. 3, 2021 (Eleven (11) pages).

Ting et al., "Preparation of 10W/40 Lube Oil for Four Stroke Engine Motorcycle", *Petroleum Processing and Petrochemicals*, vol. 30, Issue 8, Aug. 31, 1999, pp. 24-28, Chinese-language document.

Lihua Wang, "Development of Additive Package for SJ Grade Gasoline Engine Oil", *Petroleum Processing and Petrochemicals*, vol. 37, Issue 1, Jan. 31, 2006, pp. 55-58, Chinese-language document, with English Abstract.

Shirong Zhang "Development of Heavy-Duty Diesel Engine Oil CF-4 20W/50", *Qilu Petrochemical Technology*, vol. 32, Issue 03, Aug. 31, 2004, pp. 162-164, Chinese-language document.

* cited by examiner

METHOD AND SYSTEM FOR CHECKING AN OIL FOR AN INTERNAL COMBUSTION ENGINE, IN PARTICULAR OF A MOTOR VEHICLE

CROSS REFERENCE TO RELATED APPLICATIONS

This application is a continuation of PCT International Application No. PCT/EP2018/073347, filed Aug. 30, 2018, which claims priority under 35 U.S.C. § 119 from German Patent Application No. 10 2017 216 729.7, filed Sep. 21, 2017, the entire disclosures of which are herein expressly incorporated by reference.

BACKGROUND AND SUMMARY OF THE INVENTION

The invention relates to a method and a system for checking an oil as a lubricant for an internal combustion engine, in particular of a motor vehicle.

US 2011/0003725 A1 discloses a lubricating oil which is configured as a mixture with a base oil component which comprises a urea adduct value of 4% by mass or less.

Moreover, US 2006/0027486 A1 has disclosed a multiple-component engine oil which complies with the SAE J300 specifications.

It is known from the general prior art, in particular, that oils which are used as a lubricant for internal combustion engines are usually characterized by way of their viscosity and/or their shear rate at a predefined temperature. Here, the check as to whether an oil is suitable as an effective and efficient lubricant for lubricating the internal combustion engine is very intensive in terms of time and costs within the context of the development of an internal combustion engine, since a multiplicity of oils are usually checked. After the checking, at least one of the oils is selected if it has proved to be suitable.

It is therefore an object of the present invention to provide a method and a system, by means of which an oil can be checked with regard to its suitability as a lubricant for an internal combustion engine in a manner which is particularly favorable in terms of time and costs, and the oil can be selected from a multiplicity of oils.

A first aspect of the invention relates to a method for checking an oil, also called lubricating oil, as a lubricating medium for an internal combustion engine. As will be described even more precisely in the following text, it is possible by means of the method according to the invention, in particular, for the oil to be checked with regard to its suitability as a lubricant for an internal combustion engine in a manner which is particularly favorable in terms of time and costs, and for the oil to be selected for example from a multiplicity of oils. The method according to the invention comprises a first step, in the case of which at least one laboratory test is carried out. The laboratory test is to be understood to mean a test or a first checking method which is carried out independently of an internal combustion engine, that is to say without an internal combustion engine and therefore not by means of a test rig. It is therefore provided within the context of the laboratory test that at least one three-dimensional temperature/viscosity/shear rate characteristic diagram which characterizes the oil is determined independently of an internal combustion engine, that is to say without the use of an internal combustion engine. The temperature/viscosity/shear rate characteristic diagram is also called first characteristic diagram hereinbelow. The viscosity/shear rate characteristic diagram comprises a plurality of viscosities, shear rates and temperatures of the oil which are determined experimentally by means of the laboratory test and without the use of an internal combustion engine, the first characteristic diagram assigning in each case precisely one of the shear rates and precisely one of the viscosities to the respective temperatures.

Therefore, the first characteristic diagram comprises precisely one association per temperature, per shear rate and per viscosity, within the context of which association precisely one of the temperatures is assigned precisely one of the shear rates and precisely one of the viscosities, with the result that the viscosity which is assigned to the corresponding temperature is assigned to the shear rate which is assigned to the temperature, and vice versa. The laboratory test is carried out, for example, in such a way that the respective temperature of the oil is set, and the viscosity and the shear rate of the oil are determined at the respective set temperature. The viscosity which is determined at the set temperature and the shear rate which is determined at the set temperature are assigned to the set temperature. Since, within the context of the laboratory test, a plurality of temperatures of the oil are set, and the oil has different shear rates and different viscosities, for example, at different temperatures, the three-dimensional first characteristic diagram results from the temperatures and the associated shear rates and the associated viscosities. In particular, the first characteristic diagram can be represented as a hypersurface of a three-dimensional space which is defined, for example, along a first direction by way of the temperatures, along a second direction which runs perpendicularly with respect to the first direction by way of the shear rates, and along a third direction which runs perpendicularly with respect to the first direction and perpendicularly with respect to the second direction by way of the viscosities.

Furthermore, the method according to the invention comprises a second step, in the case of which a check is made as to whether the first characteristic diagram satisfies at least one predefinable criterion. The first criterion comprises, for example, that at least one of the shear rates and/or at least one of the viscosities and/or a predefinable number of shear rates and/or a predefinable number of viscosities of the first characteristic diagram does or do not exceed a respective predefinable first limit value and lies or lie below the respective first limit value.

If, for example, the first characteristic diagram satisfies the first criterion, this can be used as an indication of the fact that the oil which is checked by means of the method might fundamentally be suitable for being used as a lubricant for lubricating the internal combustion engine.

Therefore, the method according to the invention comprises a third step which is carried out when and preferably only when the first characteristic diagram satisfies the first criterion. In the case of the third step of the method, at least one test rig experiment is carried out by means of at least one internal combustion engine, in the case of which test rig experiment a check is made by means of the at least one internal combustion engine as to whether the oil satisfies at least one predefinable second criterion. Within the context of the third step, for example, an internal combustion engine is operated, in particular in an externally driven and/or combustion manner, while the internal combustion engine which is configured, for example, as a reciprocating piston engine is lubricated by means of the oil which is being checked. The second criterion comprises, for example, that the oil has lubricating properties which are such that, for example, a power consumption of the internal combustion engine and/ or an energy consumption of the internal combustion engine and/or a variable which characterizes an internal friction of the internal combustion engine and/or a fuel consumption of the internal combustion engine do/does not exceed a pre-definable second limit value or remain/remains below the second limit value, that is to say undershoot/undershoots the second limit value. If it is determined within the context of the third step that the oil satisfies the second criterion, the oil satisfies, as it were, the first criterion and the second criterion, since the first characteristic diagram characterizes the oil. If both the first criterion is satisfied in the case of the second step and the second criterion is satisfied in the case of the third step, the oil is fundamentally suitable for lubricating the internal combustion engine effectively and efficiently, with the result that, for example, an energy consumption or the fuel consumption of the internal combustion engine can be kept within a particularly low limit. In other words, it can be determined in a simple and inexpensive way by means of the method according to the invention whether efficient, in particular combustion, operation of the internal combustion engine, which operation is favorable in terms of the degree of efficiency and/or has a low fuel consumption, can be realized by means of the oil.

Here, the invention is based, in particular, on the following finding: the use of high quality oils which are also called engine oils or lubricating oils for lubricating internal combustion engines has been shown to be advantageous, in order to reduce the internal friction of the respective internal combustion engine and, as a consequence, to save fuel. It is usually necessary to carry out comprehensive and complex functional tests for a respective type of internal combustion engine, in order to determine the suitability and efficiency of the respective type with regard to the use as a lubricant for lubricating the respective type. To this end, the internal combustion engine which is also called a combustion engine is usually operated in a standard test cycle on a roller dynamometer while the internal combustion engine is being lubricated with the oil to be checked. Here, a fuel consumption of the internal combustion engine is determined, the suitability and/or the quality of the respective oil being derived from the fuel consumption. The costs for a test of this type are approximately 20 000 Euro, a test of this type taking approximately one week. Therefore, any arbitrary oil cannot be tested for its suitability for use as a lubricant for time and economic reasons, with the result that a preliminary selection is usually carried out merely qualitatively. As a result, oils which would actually be very satisfactorily suitable as an efficient and effective lubricant can already be denied the suitability as a lubricant within the scope of the preliminary selection.

It is then possible by means of the method according to the invention to check a multiplicity of oils in a manner which is favorable in terms of time and costs, in particular with regard to their suitability as a lubricant for an internal combustion engine type. It is the fundamental concept of the invention here not to replace test rig experiments completely by way of laboratory tests, but rather to combine the described laboratory test with the described test rig experiment. Here, the laboratory test according to the invention is a laboratory test method which is favorable in terms of costs and time for determining the quality and/or suitability of the oil or of oils. Since, in the case of the method according to the invention, the test rig experiment is carried out after the laboratory test and, in particular, only when the first characteristic diagram satisfies the first criterion, the test rig experiment per se can also be carried out in a manner which is favorable in terms of time and costs, and/or the number of test rig experiments to be carried out can be kept particularly low, for example, within the context of a check and selection of a plurality of oils, since the respective test rig experiment is carried out when and only when the respective first characteristic diagram satisfies the first criterion.

The laboratory test method within the context of the method according to the invention is preferably a UHSV (ultra high shear viscosity) measurement. The determined shear rates, viscosities and temperatures are measured results which are obtained by way of the laboratory test. The abovementioned hypersurface can be generated from the measured results, in the case of which hypersurface the viscosity is plotted against the temperature and the shear rate. Conclusions about the suitability of the oil with regard to the effective and efficient lubrication of the internal combustion engine can be drawn, for example, from an interpretation of the hypersurface, and can be correlated with results from the test rig experiment. Therefore, for example, the test rig experiment is a test method for verifying the laboratory test. Here, a few correlation measurements which are to be carried out within the context of the test rig experiment allow it to be possible for any fuel saving potentials which have been identified in the laboratory test to be derived on the development side without a further engine test subsequently to the laboratory test.

The laboratory test is therefore not intended to replace the test rig experiment, but rather to supplement it, in order for it to be possible for the method overall to be carried out in an manner which is favorable in terms of time and costs, and in order for it to be possible in the process for a multiplicity of oils to be checked. The main use or main purpose of the laboratory test is, for example, a preliminary selection of possible oils, without it being necessary, however, for oils to be ruled out prematurely. Potentially suitable oils can be tested further and validated or verified in the case of the test rig experiment subsequently to the laboratory test. Therefore, when a multiplicity of oils are to be checked, the number of test rig experiments can be kept particularly low, since only efficient oils which have already been pretested within the context of the laboratory test are subjected to the test rig experiment. Therefore, in comparison with conventional methods, a substantially greater measurement series can be carried out in a shorter time with the aid of the method according to the invention, and also with considerably lower costs. In other words, it has been found that, in comparison with only test rig experiments, the combination of laboratory test and test rig experiment is substantially more favorable in terms of time and costs. Here, a particularly great quantity of oils which are different than one another can be examined by means of the laboratory test and can be included in a test series.

In one particularly advantageous embodiment of the invention, the temperature in the first characteristic diagram lies in a range of from 20 degrees Celsius to 170 degrees Celsius inclusive, in particular in a range of from 40 degrees Celsius to 150 degrees Celsius inclusive. As a result, for example, the laboratory test can be carried out in a manner which is particularly favorable in terms of time and costs, it being possible for all relevant temperatures to be covered or checked.

A further embodiment is distinguished by the fact that the dynamic viscosity is used or determined as the viscosity. As a result, conclusions which are already significant as a result of the laboratory test can be drawn about the fundamental suitability of the oil as a lubricant for lubricating the internal combustion engine, with the result that the number of following test rig experiments can be kept particularly low when a multiplicity of oils are checked.

In order for it to be possible for the method to be carried out in a manner which is particularly favorable in terms of time and costs, it is provided in the case of a further refinement of the invention that, in order to test whether the first characteristic diagram satisfies the first criterion, the first characteristic diagram is compared with at least one reference characteristic diagram. The reference characteristic diagram characterizes, for example, an actually existing oil, by means of which the internal combustion engine can be lubricated particularly efficiently and effectively. As an alternative, it is conceivable that the reference characteristic diagram characterizes a virtual preferred oil which has particularly advantageous properties for lubricating the internal combustion engine. By way of the comparison of the first characteristic diagram with the reference characteristic diagram, the method can be carried out in a manner which is particularly favorable in terms of time and costs.

It is provided here, in particular, that, in the case of the comparison of the first characteristic diagram with the reference characteristic diagram, a difference is determined, in particular calculated, between the first characteristic diagram and the reference characteristic diagram. As a result, the comparison can be carried out in a manner which is particularly favorable in terms of time and costs.

It has been shown to be particularly advantageous, furthermore, if the difference is determined as a three-dimensional differential characteristic diagram. On the basis of the three-dimensional differential characteristic diagram, the first characteristic diagram and the reference characteristic diagram can be contrasted in a particularly clear manner, with the result that strengths and weaknesses of the oil to be checked in comparison with the preferred oil can be visualized and therefore can be detected particularly simply, for example, on the basis of the three-dimensional differential characteristic diagram.

A known lubricating oil is used, for example, instead of the preferred oil or as the preferred oil. As a consequence, it is possible, for example, to use the comparison of the oil to be checked with the known lubricating oil in order to check the identity of oils. On the basis of the differential characteristic diagram, for example, any differences between the oil to be checked and the known lubricating oil can be determined. In other words, it can be determined on the basis of the differential characteristic diagram whether the oil to be checked differs from the known lubricating oil. If, for example, the oil to be checked does not differ from the known lubricating oil or any differences lie within certain limits, it can be concluded that the oil to be checked corresponds to the known lubricating oil (preferred oil). If, however, the oil to be checked differs from the known lubricating oil, for example, or the differences lie outside the limits, it can be concluded that the oil to be checked is an oil which is different than the known lubricating oil. In this way, for example, the or an identity of the oil to be checked can be determined, in particular at least qualitatively.

Finally, it has been shown to be particularly advantageous if, by means of the method according to the invention, at least one of the oils is selected from a plurality or multiplicity of oils which are different than one another on the basis of the fact that the first characteristic diagram of the at least one oil satisfies the first criterion and on the basis of the fact that the at least one oil satisfies the second criterion, and the at least one of the oils is selected as a lubricant for the internal combustion engine. The oils to be checked are each subjected to a laboratory test, for example. Of the plurality of oils, only that oil is or only those oils are subjected to the test rig experiment, the first characteristic diagram or first characteristic diagrams of which satisfies or satisfy the first criterion. Therefore, for example, the number of test rig experiments to be carried out can be kept low in comparison with the number of oils to be checked, with the result that the method overall can be carried out in a manner which is favorable in terms of time and costs, and the oils can be checked in a manner which is particularly favorable in terms of time and costs. If, for example, a plurality of oils satisfy both the first criterion and the second criterion, that oil which, in comparison to the respective other oils, brings about or makes possible a sufficient lubrication and, at the same time, a low fuel consumption of the internal combustion engine is selected from the oils.

A second aspect of the invention relates to a system for carrying out a method according to the invention; advantages and advantageous refinements of the system according to the invention are to be considered to be advantages and advantageous refinements of the method according to the invention, and vice versa.

Further details of the invention result from the following description of one preferred exemplary embodiment with the associated drawings.

Other objects, advantages and novel features of the present invention will become apparent from the following detailed description of one or more preferred embodiments when considered in conjunction with the accompanying drawings.

DETAILED DESCRIPTION OF THE DRAWINGS

In the Figures, identical or functionally identical elements are provided with identical designations.

Figure 1:
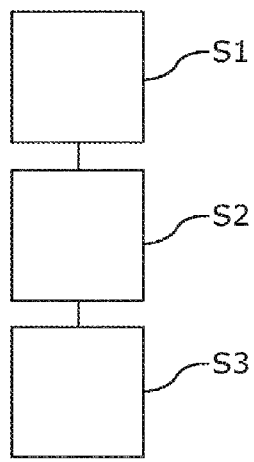
FIG. 1 shows a flow chart for illustrating a method according to the invention for checking an oil as a lubricant for an internal combustion engine.
Figure 2:
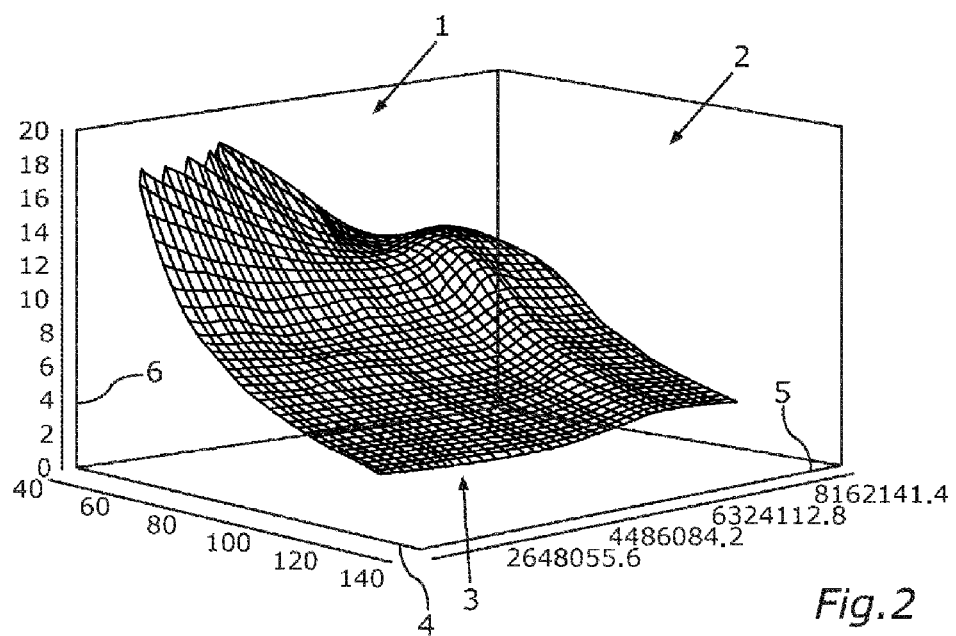
FIG. 2 shows a three-dimensional temperature/viscosity/shear rate characteristic diagram of a first oil.

FIG. 1 shows a flow chart for illustrating a method for checking at least one oil as a lubricant for an internal combustion engine. In a first step S1 of the method, at least one laboratory test is carried out independently of an internal combustion engine, that is to say without an internal combustion engine, in the case of which laboratory test a three-dimensional temperature/viscosity/shear rate characteristic diagram which characterizes the oil is determined independently of an internal combustion engine, that is to say without using an internal combustion engine. FIG. 2 shows a temperature/viscosity/shear rate characteristic diagram of this type of an oil, which characteristic diagram is determined by means of the laboratory test, and the characteristic diagram is denoted by 1 there. The temperature/viscosity/shear rate characteristic diagram 1 comprises a plurality of viscosities, shear rates and temperatures of the oil to be checked which are determined experimentally by means of the laboratory test, and assigns the respective temperatures in each case precisely one of the shear rates and precisely one of the viscosities. The determined viscosities are to be understood to mean, for example, viscosity values which characterize, for example, a viscosity, in particular the dynamic viscosity, of the oil at the plurality of temperatures which are different than one another and are set, for example, within the context of the laboratory test. The respective shear rates are, for example, respective shear rate values which characterize, for example, a shear rate of the oil at the temperatures which are set. The temperatures, for example, are then temperature values which are different than one another, with the result that each of the temperature values of the temperature/viscosity/shear rate characteristic diagram is assigned precisely one of the shear rate values and precisely one of the viscosity values.

The temperature values, the shear rate values and the viscosity values are also collectively called values. Plotted on a diagram 2 which is shown in FIG. 2 and linked to one another, the values result, for example, in a hypersurface 3 which can be seen in FIG. 2 in a three-dimensional space which is defined along a first direction by way of the temperature, along a second direction which runs perpendicularly with respect to the first direction by way of the shear rate, and along a third direction which runs perpendicularly with respect to the first direction and perpendicularly with respect to the second direction by way of the viscosity. In other words, the hypersurface 3 illustrates or visualizes the temperature/viscosity/shear rate characteristic diagram 1 which is also called a first characteristic diagram. Here, the diagram 2 has a first axis 4, on which the temperatures or temperature values are plotted. Furthermore, the diagram 2 has a second axis 5 which runs perpendicularly with respect to the first axis 4 and on which the shear rates or shear rate values are plotted. Finally, the diagram 2 has a third axis 6 which runs perpendicularly with respect to the first axis 4 and perpendicularly with respect to the second axis 5 and on which the viscosities or viscosity values are plotted. Therefore, the viscosity which is, in particular, dynamic is plotted against the temperature and the shear rate in the case of the hypersurface 3.

In a second step S2 of the method, a check is carried out, for example, as to whether the temperature/viscosity/shear rate characteristic diagram 1 satisfies at least one predefinable criterion. The first criterion comprises, for example, that at least one or a plurality of the viscosities of the first characteristic diagram undershoots or undershoot a predefinable first limit value.

If the temperature/viscosity/shear rate characteristic diagram 1 satisfies the first criterion, a third step S3 of the method is then carried out and, in particular, is carried out only then. In the third step, at least one test rig experiment is carried out which is carried out with the aid of an internal combustion engine. In the case of the test rig experiment, a check is therefore made by means of an internal combustion engine as to whether the oil, the temperature/viscosity/shear rate characteristic diagram of which satisfies the first criterion, satisfies at least one predefinable second criterion. In the case of the test rig experiment, for example, a fuel consumption of the internal combustion engine is determined. The second criterion comprises, for example, that the fuel consumption undershoots a predefinable second limit value. If the fuel consumption undershoots the predefinable second limit value, a conclusion can be drawn that the oil has an advantageous lubricating capability which is such that the fuel consumption is below the second limit value. Since the oil therefore as it were satisfies both the first criterion and the second criterion, a conclusion can be drawn that the oil is fundamentally suitable for it to be possible for the internal combustion engine to be lubricated sufficiently and in the process at the same time for the fuel consumption to be kept particularly low.

Figure 3:
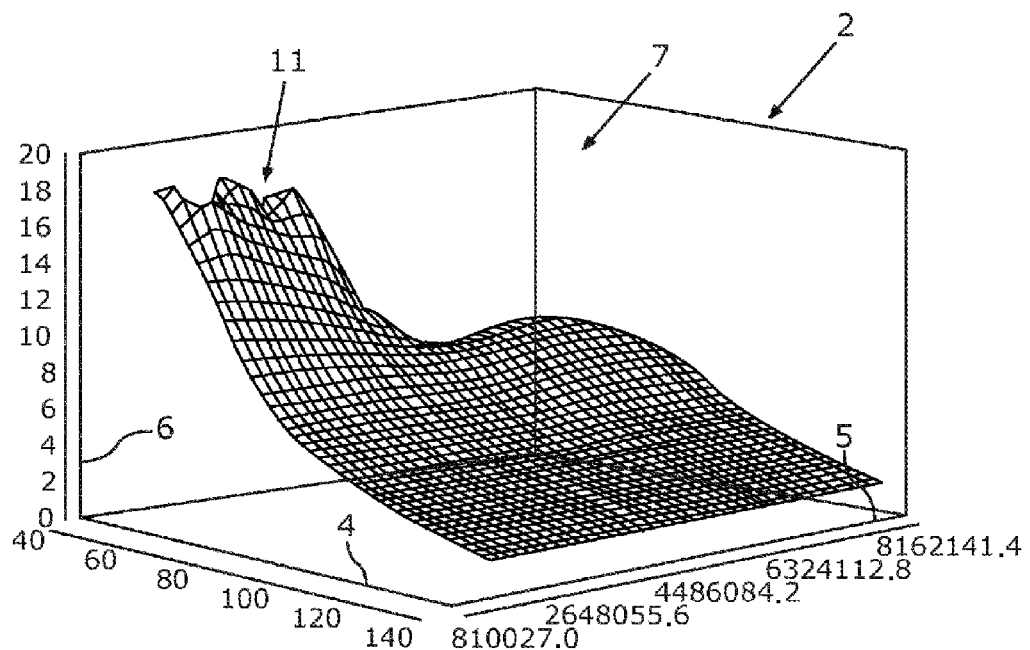
FIG. 3 shows a three-dimensional temperature/viscosity/shear rate characteristic diagram of a second oil.

FIG. 3 shows a temperature/viscosity/shear rate characteristic diagram 7 of a second oil. It can be recognized on the basis of the temperature/viscosity/shear rate characteristic diagram 7 that the second oil has a high viscosity at low temperatures and low shear rates in comparison with the oil which is also called the first oil and the temperature/viscosity/shear rate characteristic diagram 1 of which is shown in FIG. 2. In particular, FIG. 3 shows a hypersurface 11 of the temperature/viscosity/shear rate characteristic diagram 7. It can be seen here from FIGS. 2 and 3 that the temperature in the respective temperature/viscosity/shear rate characteristic diagram 1 and 7, respectively, lies in a range of from 40 degrees Celsius to 150 degrees Celsius. Furthermore, the dynamic viscosity is used as the viscosity.

Figure 4:
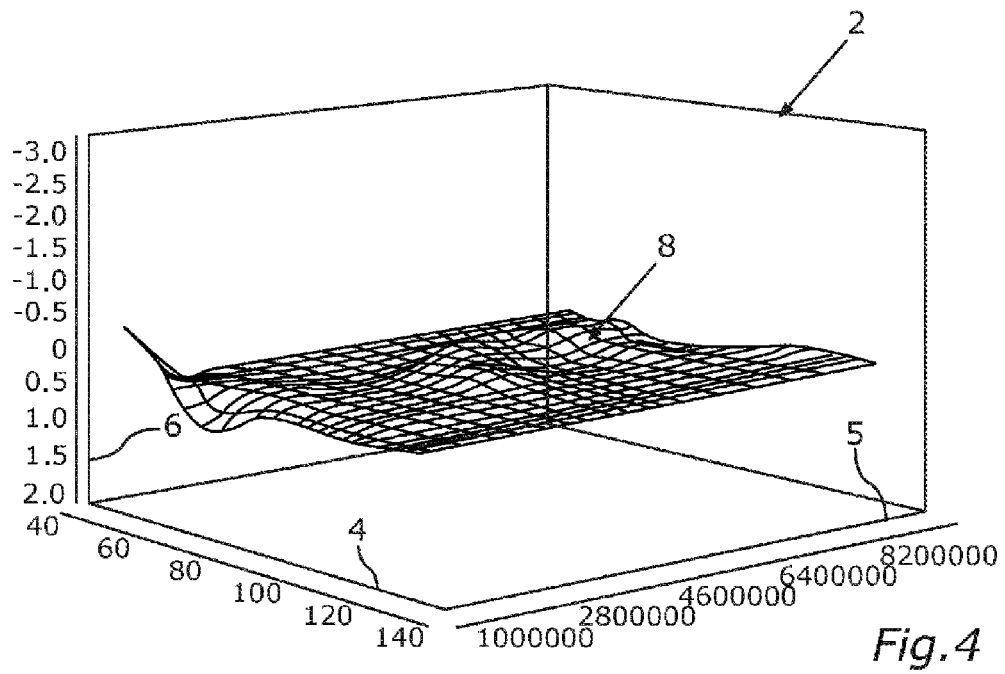
FIG. 4 shows a first three-dimensional differential characteristic diagram.

In order to check whether the temperature/viscosity/shear rate characteristic diagram 1 and 7 satisfies the first criterion, the temperature/viscosity/shear rate characteristic diagram, for example, is compared with at least one reference characteristic diagram, in particular in such a way that the difference in the form of a three-dimensional differential characteristic diagram is determined between the temperature/viscosity/shear rate characteristic diagram 1 and 7 and the reference characteristic diagram. A three-dimensional differential characteristic diagram of this type is shown in FIG. 4 and is denoted there by 8. The reference characteristic diagram is, for example, a temperature/viscosity/shear rate characteristic diagram of a known oil which is also called a reference oil, has, for example, particularly advantageous properties, and the sort or type or identity of which is known. It can be seen rapidly and simply from the differential characteristic diagram 8 that the lubricating oil to be checked has improved lubricating properties in comparison with the reference oil and therefore leads to fuel savings, in particular in the case of the test rig experiment.

Figure 5:
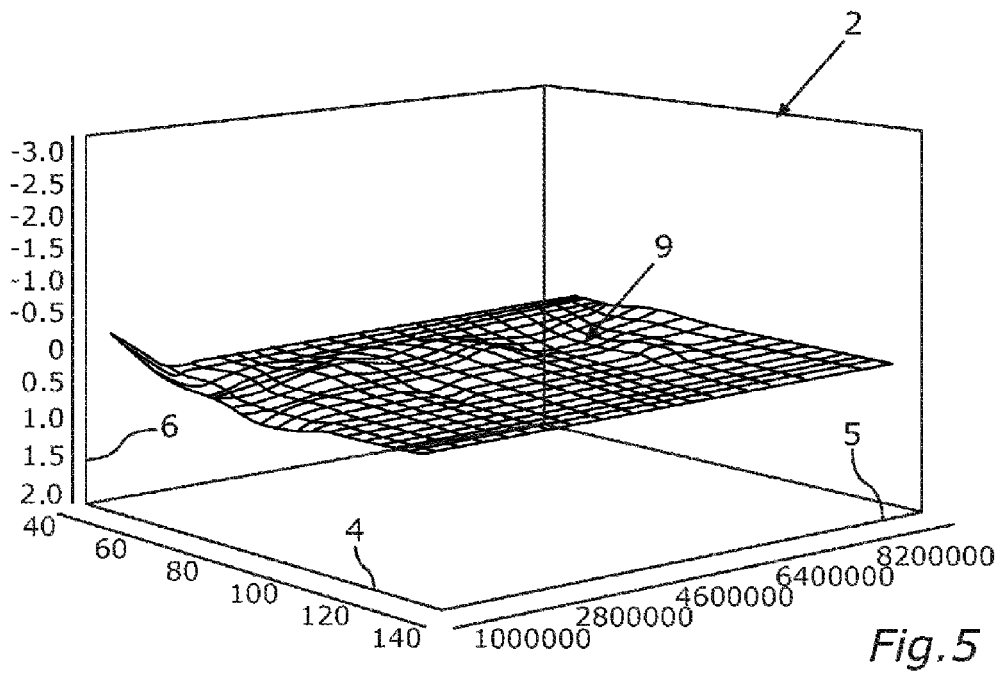
FIG. 5 shows a second three-dimensional differential characteristic diagram.

FIG. 5 shows a three-dimensional differential characteristic diagram 9. It can be seen on the basis of the differential characteristic diagram 9 that the reference oil and the oil to be checked are equivalent, with the result that the reference oil and the oil to be checked lead to an at least approximately identical fuel consumption in the case of the test rig experiment.

Figure 6:
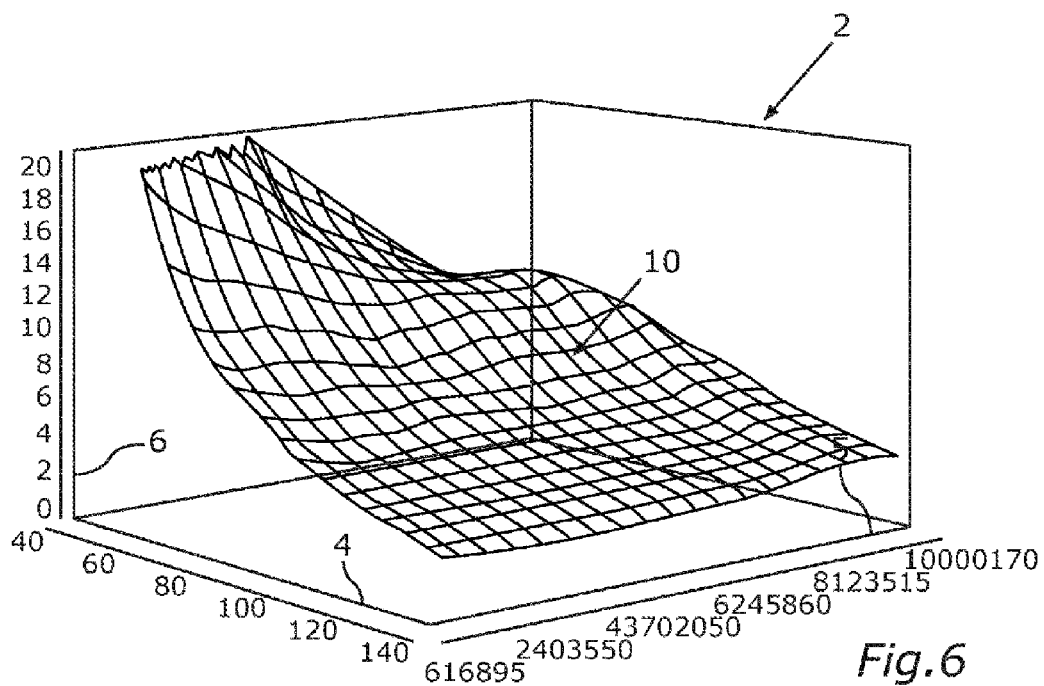
FIG. 6 shows a third three-dimensional differential characteristic diagram.

Finally, FIG. 6 shows a third differential characteristic diagram 10. It can be seen on the basis of the three-dimensional differential characteristic diagram 10 that the oil to be checked has poorer lubricating properties in comparison with the reference oil, and therefore leads to an increased fuel consumption, in particular in the case of the test rig. Overall, the method makes it possible to select the oil or the oils from a multiplicity of oils to be checked in a way which is favorable in terms of time and costs, which oil or oils is/are suitable for lubricating the internal combustion engine sufficiently and in the process keep the fuel consumption low. Here, only those ones of the oils, the temperature/viscosity/shear rate characteristic diagram of which satisfies the first criterion, are subjected to the respective test rig experiment. As a result, the number of test rig experiments to be carried out can be kept particularly low, with the result that the oil or the oils can be identified rapidly and inexpensively, can be selected, and can then be utilized, for example, as a lubricant for lubricating the internal combustion engine.

LIST OF REFERENCE CHARACTERS

1 Temperature/viscosity/shear rate characteristic diagram
2 Diagram
3 Hypersurface
4 Axis
5 Axis
6 Axis
7 Temperature/viscosity/shear rate characteristic diagram
8 Differential characteristic diagram
9 Differential characteristic diagram
10 Differential characteristic diagram
11 Hypersurface The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for checking an oil as a lubricating medium for an internal combustion engine, comprising the acts of:
   carrying out of a laboratory test of the oil without use of the internal combustion engine and therefore without use of a test rig and producing a three-dimensional temperature/viscosity/shear rate characteristic diagram based on the laboratory test, wherein the three-dimensional temperature/viscosity/shear rate characteristic diagram comprises a plurality of viscosities, shear rates and temperatures of the oil which are determined experimentally by the laboratory test and wherein precisely one of the shear rates and precisely one of the viscosities are assigned to a respective temperature;
   testing of whether the three-dimensional temperature/viscosity/shear rate characteristic diagram satisfies a predefinable first criterion; and
   only when the three-dimensional temperature/viscosity/shear rate characteristic diagram satisfies the predefinable first criterion, carrying out of a test rig experiment in which a check is carried out using the internal combustion engine as to whether the oil satisfies a predefinable second criterion.

2. The method according to claim 1, wherein the respective temperatures in the three-dimensional temperature/viscosity/shear rate characteristic diagram lie in a range of from 20 degrees Celsius to 170 degrees Celsius.

3. The method according to claim 1, wherein respective dynamic viscosities are used for the plurality of viscosities.

4. The method according to claim 1, wherein in the testing of whether the three-dimensional temperature/viscosity/shear rate characteristic diagram satisfies the predefinable first criterion, the three-dimensional temperature/viscosity/shear rate characteristic diagram is compared with a reference characteristic diagram.

5. The method according to claim 4, wherein when the three-dimensional temperature/viscosity/shear rate characteristic diagram is compared with the reference characteristic diagram, a difference is determined between the three-dimensional temperature/viscosity/shear rate characteristic diagram and the reference characteristic diagram.

6. The method according to claim 5, wherein the difference is determined as a three-dimensional differential characteristic diagram.

7. The method according to claim 1 further comprising the act of selecting the oil as the lubricating medium for the internal combustion engine on a basis that the predefinable first criterion and the predefinable second criterion are satisfied.

8. A system for carrying out the method according claim 1.

* * * * *